United States Patent [19]

Rudin

[11] 4,208,588
[45] Jun. 17, 1980

[54] HAND-HELD SHIELDING DEVICE FOR RADIOACTIVE MATERIAL

[75] Inventor: Stephen Rudin, Williamsville, N.Y.

[73] Assignee: Victoreen, Inc., Cleveland, Ohio

[21] Appl. No.: 842,131

[22] Filed: Oct. 14, 1977

Related U.S. Application Data

[63] Continuation-in-part of Ser. No. 617,022, Sep. 26, 1975, abandoned.

[51] Int. Cl.² .................. G21F 5/00; A61N 5/00
[52] U.S. Cl. .................. 250/496; 250/497; 128/1.1; 128/215
[58] Field of Search .......... 128/1.1, 1.2, 2 A, 215; 250/506, 497, 496

[56] References Cited

U.S. PATENT DOCUMENTS

| | | | |
|---|---|---|---|
| 831,103 | 9/1906 | Ripperger | 250/496 X |
| 2,594,970 | 4/1952 | Monk | 250/506 |
| 3,102,958 | 9/1963 | King | 250/506 X |
| 3,265,584 | 8/1966 | Cooper | 250/496 X |
| 3,673,411 | 6/1972 | Glasser | 250/506 |

OTHER PUBLICATIONS

Ter-Pogossian et al., "Handling of Radioactive Gold for Therapeutic Purposes," *Nucleonics*, vol. 10, No. 3, Mar. 1952.

*Primary Examiner*—Clifford D. Crowder
*Attorney, Agent, or Firm*—Blum, Kaplan, Friedman, Silberman & Beran

[57] ABSTRACT

A hand-held shielding device for holding and viewing a container of radioactive material is provided. The device comprises an elongated holding portion for the container formed with a longitudinal aperture therein and a shielding portion overlapping the aperture for shielding against direct radiation through the aperture. Indirect optical imaging is provided on the shielding portion for viewing the container and material therein at a viewing position away from direct radiations emanating through the aperture.

13 Claims, 9 Drawing Figures

HAND-HELD SHIELDING DEVICE FOR RADIOACTIVE MATERIAL

CROSS REFERENCE TO RELATED APPLICATION

This is a continuation-in-part of application Ser. No. 617,022 filed Sept. 26, 1975 and now abandoned.

BACKGROUND OF THE INVENTION

This invention relates to shielding devices for containers of radioactive materials and more particularly for devices used during the handling and measuring of material emitting high energy electromagnetic and/or particulate radiation such as gamma or beta radiation.

Because of the high energy of the radiation from materials presently used in radiation therapy and diagnosis, it is necessary to enclose such materials within radiation attenuating shields.

At present, for example, a commonly used radiation material is Technetium 99m ($^{99m}Tc$) which is a strong gamma-radiating source. The material is routinely used in solution and is administered by hypodermic injection. Because of the high energies of the radiation of the material it is necessary to protect the personnel handling and administering these solutions. Such personnel require protection since they are repeatedly exposed to the radiation during the preparation of the solutions, the standardization procedures, dosage division and measurement and during administration. It is known to provide tubular shielding holders for the usual cylindrical containers of the radioactive materials. U.S. Pat. No. 3,820,541 shows such a holder for a hypodermic syringe. Such holders have the disadvantage of not permitting viewing of the contents of the containers and thus preclude direct measurement by observation or the ability to both observe and manually control the manipulation of the solutions during preparation, transfer to vials, standardization and dosage measurement into hypodermic syringes.

Recently these tubular shielded holders have been modified, as taught in U.S. Pat. No. 3,596,659 and its continuation-in-part U.S. Pat. No. 3,673,411 by utilizing an opening in the cylindrical shield to permit visual observation of the scales on the hypodermic syringe (U.S. Pat. No. 3,596,659) or the contents of multiple dose containers (U.S. Pat. No. 3,673,411). This opening in the shield is filled with a high density lead glass to attenuate the radiation escaping through the opening. While this permits observation for the manipulation and measurement of the contents of the container in the holder, one disadvantage is that even using the highest density lead glass window available, the attenuated radiation which still emanates from the shielded holder through this viewing glass is high enough to provide a potential hazard particularly to the eyes of personnel engaged in measuring operations as they must position their eyes directly in the line of the emanating radiation in order to reduce parallax errors and to the fingers and hands from such radiation through the windows when the shield is being held. This disadvantage is even more pronounced when used with other higher energy radiation materials requiring shielding during handling such as $131_I$, $67_{Ga}$ and $80m_{Br}$ as well as positron annhilation radiation emitters such as the cyclotron generated positron emitting isotopes of Carbon, Nitrogen and Oxygen. Also commonly or experimentally used are the radioactive isotopes of thallium and rubidium and the standards such as $137_{Cs}$.

Another disadvantage is that the leaded glass is easily broken. Further, the shield is heavy and thus has disadvantages during use.

The March, 1952 issue of Nucleonics shows a shielded syringe having a shielding jacket surrounding a syringe with a thin lengthwise slit in the jacket for observation of the scale on the syringe by means of a mirror held apart and opposite from the slit. Illumination to permit viewing of the syringe is provided by an electric light inside the device. The device shown is heavy and bulky and is mounted to a base member for holding the remote syringe. This inherent bulkiness of the device combined with the facts tht the light for illuminating the syringe must be connected to a power source and that no shielding is provided between the shielding jacket and mirror and behind the mirror, prevents the device from being utilized as a hand-held device for administering small doses of radioactive material. This latter point is significant as a syringe must be raised to eye level to read accurately the scale markings on a syringe This raises serious health problems for a user as the effects of exposure to radiation are cumulative and especially so in the region of the eyes. In addition, the device includes a long length of tubing which is unshielded between the device and needle.

Accordingly, it would be desirable to provide a shielding device which would offer maximum protection from radiation yet be suitable for hand-held direct dispensing of small dosages of radioactive material.

SUMMARY OF THE INVENTION

Generally speaking, in accordance with the invention, a hand-held shielding device for holding and viewing a container of radioactive material, comprising a holding portion and a shielding portion formed from a high density radiation shielding material of essentially spiral cross-section is provided. The holding portion is shaped to surround and conform to the configuration of the container desired to be observed and is formed with a longitudinally extending aperture extending for at least a portion of the length of the high density material. The shielding portion extends integrally from one side of the aperture and extends away from and over the line of sight through the aperture. An indirect optical imaging means is provided between the aperture and the shielding portion to permit viewing of the container through the aperture. Thus, the interior of the container and its contents are under indirect visual observation without exposure of the eyes or other organs to gamma and beta radiation emanating from the aperture.

Accordingly, it is an object of the invention to provide an improved radiation shielding device.

Another object of the invention is to provide a hand-held radiation shielding device of improved design.

A further object of the invention is to provide a shielding device for containers for radioactive materials which permits viewing the contents thereof during preparation, manipulation, transfer, assay measurement and administration which overcomes the disadvantages of the prior art devices.

Still another object of the invention is to reduce the amount of radiation escaping from holders provided with viewing windows.

Still a further object of my invention is to provide a device which is lightweight, resistant to breakage, economical to manufacture and is easily standardized so as to be available for interchangeable use with disposable hypodermic syringes and is sufficiently economical to be retired for decontamination or repair when accidentally contaminated or deformed.

The invention accordingly comprises an article of manufacture possessing the features, properties, and the relation of elements which will be exemplified in the article hereinafter described, and the scope of the invention will be indicated in the claims.

Still other objects and advantages of the invention will in part be obvious and will in part be apparent from the specification.

BRIEF DESCRIPTION OF THE DRAWINGS

For a fuller understanding of the invention, reference is had to the following description taken in connection with the accompanying drawings, in which.

DETAILED DESCRIPTION OF THE PRESENT INVENTION

Figure 1:
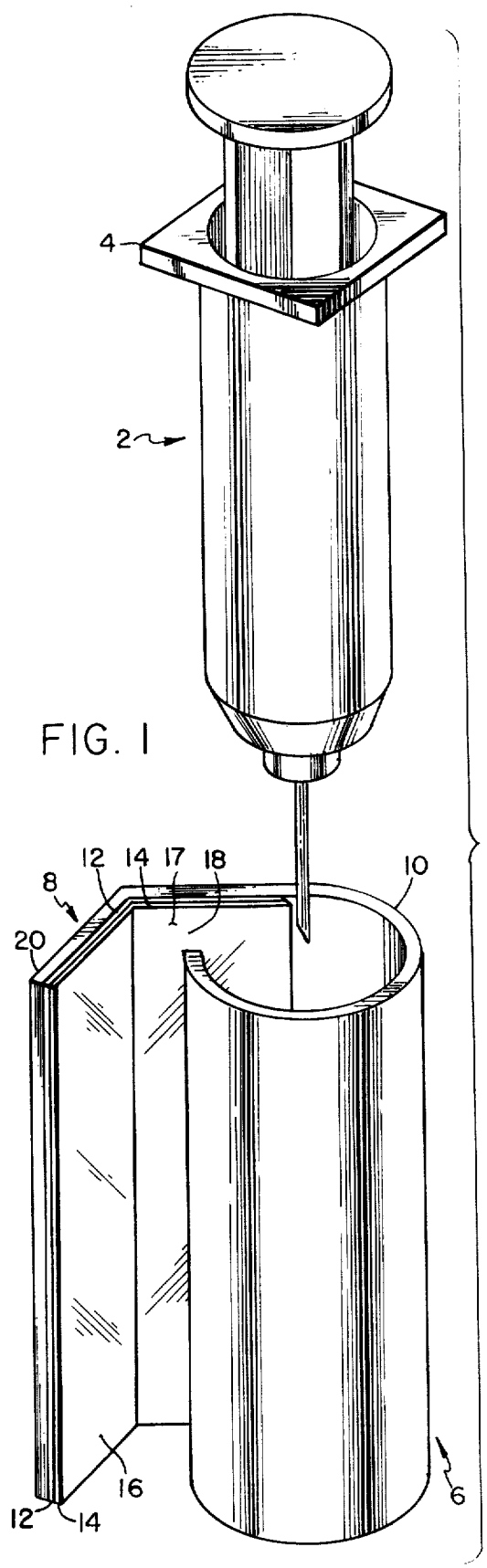
FIG. 1 is a perspective view of one embodiment of the shielding device of the present invention.

FIG. 1 shows a shielding device constructed and arranged in accordance with the invention. A shielding device shown generally as 6 includes a holding portion 10 which is receptive of a container, such as a hand-operated syringe 2. Holding portion 10 is formed from a high density radiation shielding material to shield against radiations emanating from radioactive material in syringe 2. Syringe 2 normally has indicia thereon to indicate the volume of the substance therein and it is desired to observe these indicia or the level of the substance in the syringe during use of the syringe when it is in the shielding device. Thus, holding portion 10 is formed with an aperture 18 therein which in this embodiment is longitudinal and runs the entire length of holding portion 10. Aperture 18 is aligned with the indicia on the syringe and thus the indicia is visibly exposed through the aperture.

As a result of having aperture 18 formed in holding portion 10, radiations may pass through the aperture 18 and endanger the user of the shielded syringe. Thus shielding device 6 includes a shielding portion 20 which is provided to shield against direct radiation through aperture 18. Holding portion 10 and shielding portion 20 are formed from a high density shielding material such as lead, tantalum, tungsten, gold, bismuth or osmium. Shielding portion 20 is connected at one edge of aperture 18 and extends therefrom, overlapping the other edge of aperture 18 and spaced apart from holding portion 10. In order to permit the viewing of the indicia or some other desired portion of the container or syringe 2, indirect optical imaging means including reflective surfaces 16 and 17 are provided. Reflective surfaces 16 and 17 provide indirect imaging of the indicia of the syringe by providing the image of the indicia at a position for indirect viewing from a position that is away from direct radiations through aperture 18.

Indirect imaging is used herein to differentiate from direct imaging, such as through glass or some other substance where mere refraction takes place. The direct radiations follow the same path as the image, however they are not reflected but absorbed and scattered by the shielding member. In the embodiment shown, the image of the indicia is reflected on both reflective surfaces 16 and 17 so that a user can view the indicia and yet be protected from direct radiation passing through aperture 18. Shielding portion 20 which is composed of the high density shielding material absorbs most of the radiations directed thereon as explained hereinafter and thus shields the external area from direct radiation through aperture 18.

In the embodiment shown in FIG. 1, there is a double reflection so that the resulting image is not reversed. The reflecting surfaces are on the surface of a member 14 which may be a mirror comprising aluminized MYLAR, a tungsten sheet or a polished surface of the high density shielding material. In order to shield further against radiation, an intermediate layer 12 of a material such as tin may be used. As shown, holding portion 10 and shielding portion 20 are integral forming a unitary envelope of essentially spiral cross-section. The integral body may be formed of soft high density material with a laminate of rigid material. The body can also be formed from a rolled sheet of lead with or without a laminated layer of another metal or shape maintaining polymeric material.

Figure 3:
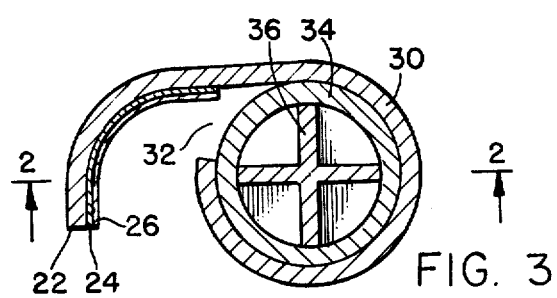
FIG. 3 is a sectional view of the device of FIG. 2.
Figure 2:
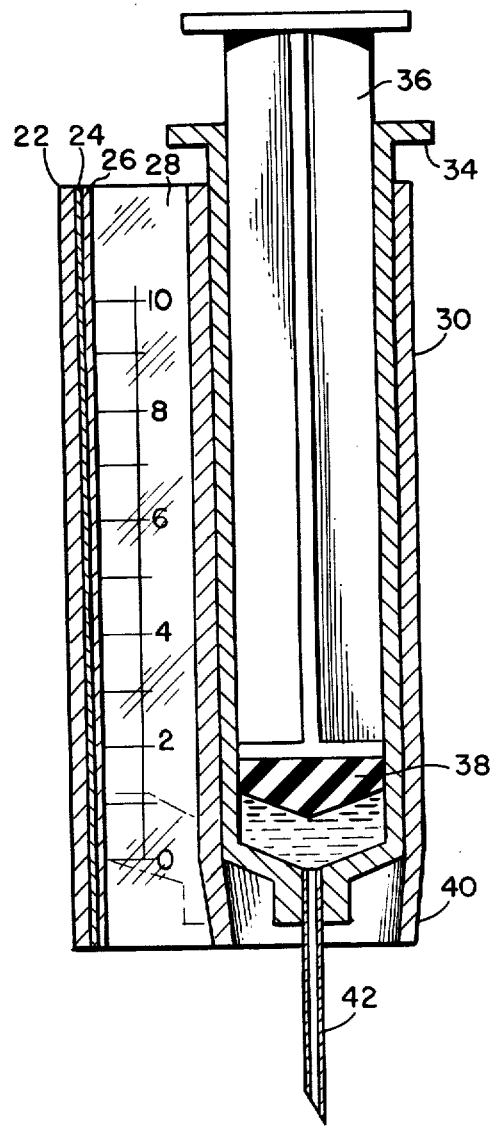
FIG. 2 is a sectional view of another embodiment of the present invention.

FIGS. 2 and 3 show another embodiment of the present invention used with a syringe including a plunger formed with an elongated stem 36 and a plug 38, and a cylindrical body 34 and a needle portion 42. In FIG. 2, holding portion 30 is shaped to surround and conform to the configuration of syringe body 34 with a longitudinally extending aperture 32 and is tapered at needle end 40 so that a combination of the spring of the metal and friction help to maintain the syringe in the shielded position inserted in the shielding device.

In this embodiment, the indirect optical imaging means includes a reflective surface 28 which is the surface of a member 26 which can be aluminized mylar or a mirror. Shielding portion 22 is arcuate in shape and member 26 and reflective surface 28 are also arcuate, resulting in an image of the syringe indicia which is not reversed. A layer 24 of lower energy radiation absorbing material such as Sn is positioned between shielding portion 22 and reflecting member 26 for selective absorption of lead emitting radiation. Successive layers of lower energy absorbing materials such as Cu and then Al also may be included for selective absorption of radiation emitted from the adjacent shielding member.

FIGS. 4-7 show embodiments of the holding member with indirect optical imaging carried out by various optical devices.

Figure 4:
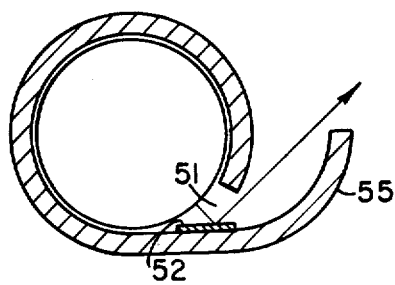
FIG. 4 is a sectional view of another embodiment of the present invention.

In FIG. 4, a shielding portion 55 is arcuate and the indirect optical imaging is carried out by a member 52 having a reflecting surface opposite an aperture 51. The resulting image is reversed when seen by the user.

Figure 5:
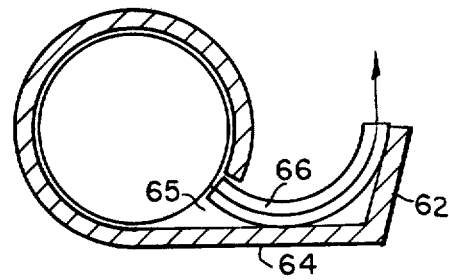
FIG. 5 is a sectional view of still another embodiment of the present invention.

In FIG. 5, a shielding portion includes two planar portions 62 and 64. The indirect optical imaging is carried out by a fiber optics 66 which transfer the image from an aperture 65 to the outside of the portion of shielding member 62.

Figure 6:
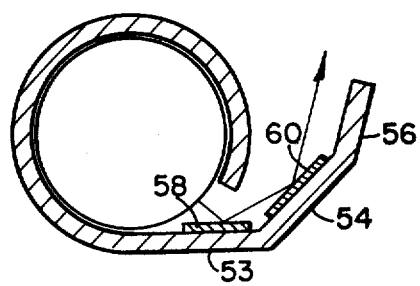
FIG. 6 is a sectional view of a further embodiment of the present invention.

In FIG. 6, a shielding portion comprises three planar surfaces 53, 54 and 56. The indirect optical imaging is carried out by two reflecting members 58 and 60 having reflecting surfaces and as a result of the double reflection, the resulting image is not reversed.

Figure 7:
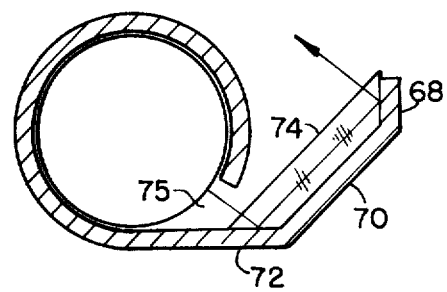
FIG. 7 is a sectional view of a still further embodiment of the present invention.

In FIG. 7, a shielding portion comprises three planar portions 68, 70 and 72 which are configured to receive a prism 74 which is preferably made out of glass or plastic and which provides a double reflection therethrough to produce the indirect optical image.

Figure 8:
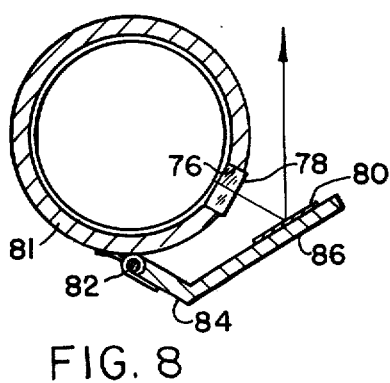
FIG. 8 is a sectional view of another embodiment of the present invention.

In FIG. 8, an embodiment is shown wherein the prior art device can be modified according to the present invention. A shielding member comprises two planar portions 84 and 86 connected to a holding portion 81 formed with an aperture 76 by a hinge 82. A reflecting member 80 having a reflecting surface is disposed on a portion 86 of the shielding member. The shielding member can then be pivotally moved to a closed position wherein aperture 76 is closed by portion 86 of the shielding member. When it is desired to observe a portion of the container in the device, the shielding portion is pivoted about hinge 82 and the user can view the container by the indirect optical imaging means including reflecting member 80 having a reflecting surface. As further protection, a leaded glass 78 can be dispersed in aperture 76. The holding means or body may be molded, machined or otherwise fashioned to hold the radioactive container. The holding body may be enclosed within a protective shape-maintaining element to prevent deformation of the soft lead that is commonly used.

In each of the embodiments shown in the drawings, it has also been found useful to put a light reflective coating on the inner surface of the holding member and the shielding member such as white paint or the like to improve the illumination of the portion of the container to be observed.

Figure 9:
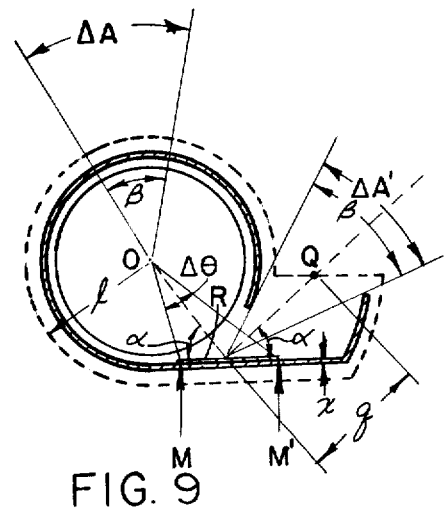
FIG. 9 is a sectional view of an embodiment of the present invention illustrated for theoretical considerations.

With reference to FIG. 9 the following is a calculation of radiation attenuation by the device of the present invention. FIG. 9 shows an embodiment of the present invention with a mirror R for the indirect optical imaging.

I. Exposure in area $\Delta A$

The attenuation is equivalent to thickness of lead x. The attenuation factor is $(e^{-\mu x})B$ where B is the "build-up" factor due to scatter in the lead (forward) and $\mu$ is the linear attenuation coefficient for the particular $E_\gamma$.

II. Exposure in area $\Delta A'$ (1.) Since the light from the container is reflected at the same angle, $\alpha$, as the incident angle $\alpha$, then the scattered gamma rays from the lead behind the mirror surface R which are of interest in determining the exposure, coming out of the container to the area $\Delta A'$ will be coming out at average angle $\alpha$ also. Thus the length of the path of the gamma rays through the lead at MM' will be skewed from the vertical.

(2.) Consider $\beta \approx 30°$ then a) since the incident gamma rays can be Compton scattered approximately equally in all directions for low energy gamma rays ($E_{65} \leq 150$ keV) according to the Klein-Nishina formula and b) since for 150 keV gamma rays almost all interaction with lead is photoelectric then the photon flux is reduced by a factor of $30/360 \approx 1/10$.

(3.) In addition the outgoing radiation is primarily 74 keV lead x-rays whose $\mu$ in lead is about the same as that for the $\sim 150$ keV incident $^{99m}$Tc radiation. The mean free paths ($\mu^{-1}$) of incoming and outgoing radiation from the lead are then about equal. This gives an additional photon flux reduction for the outgoing x-rays of $\sim 1/e$.

(4.) Since the exposure rate, X is proportional to the energy flux multiplied by the cross-section for interaction where the energy flux for monochromatic $\gamma$ or x-rays is $\phi$, the photon flux multiplied by the energy, $E_{65}$, then $$X = \phi E_\gamma (\tau \rho a) \text{ (Const.)},$$

where $\tau$ is the interaction cross-section.

$$\tau = \frac{\mu}{\rho} \times \frac{1}{\rho a}$$

where $\rho a$ = No. of atoms per gram $\mu/\rho$ = mass absorption coefficient for air $$\rho a = \frac{Av \text{ (Avogadro's No.)}}{A \text{ (Atomic weight)}}$$

Since the incident $E_{65} \approx 140$ keV on the lead MM' is about 2X the outgoing $E_x \approx 74$ keV, then the outgoing energy flux is $\frac{1}{2}$ the incoming. Thus another factor of $\frac{1}{2}$ is introduced into the attenuation factor. The total so far is $1/10 \times \frac{1}{e} \times \frac{1}{2} \approx 1/40$ for the region $\Delta A'$, compared to the area of $\Delta A$.

(5.) In addition if 0.5 mm of tin sheet (Sn) is used in between the aluminized MYLAR and the sheet lead, as shown in FIGS. 2 and 3, an additional reduction of about $\frac{1}{4}$ is introduced. The reason for this is the Sn does not attenuate the incoming 140 keV gamma rays (since the HVL for Sn is 1.67 mm for 150 keV gamma rays) where as the outgoing x-rays are heavily attenuated (since the HVL for Sn is 0.27 mm for 74 keV x-rays; hence 0.5 mm is about two HVL's giving a factor of $\frac{1}{4}$).

(6.) Finally an additional reduction of finger exposure is due to the inverse distance law. For an infinite line source the exposure goes as $1/r$. If the dotted line in FIG. 9 represents the closest position for the fingers of the operator to the syringe, then the exposure at Q, where $\Delta A'$ is, will be reduced by additional factor $1/q$ for a line source where 1 is the outside radius of the shield 6 in FIG. 9.

(7.) There will be 25 keV x-rays emitted from the Sn but since they can be emitted in all directions and only $\sim 30°$ or $\sim 1/10$ can get to $\Delta A'$, then the photon flux of 25 keV K x-rays from Sn will be:

$$(1/10 \times \tfrac{1}{4}) \Delta N \times (0.75)(0.1) \approx 0.004 \Delta N$$

where $\Delta N$ is the photon flux through the aperture $\Delta \theta$. This does not include attenuation in the Sn itself. The Sn derived radiation is negligible as compared to the scattered radiation from the lead.

EXAMPLE

The indirect optical imaging syringe shielding device is compared with a standard leaded glass window direct viewing syringe shield from two points of view. First the theoretical shielding abilities of both designs are compared by considering the geometric parameters and materials of each shield design. In particular the calculated values (for the 140 keV gamma radiation from $^{99m}$Tc) of the radiation exposure attenuation factors at points outside the shield walls and optical windows are considered. Second a shielding device with indirect viewing means was constructed to have similar shielding properties for the shield walls of a standard commercial direct viewing syringe shield and the performance of both shields for a syringe containing $^{99m}$Tc radioiostope was experimentally determined.

THEORETICAL COMPARISONS

A. Direct Viewing Shield

1. Dimensions

The dimensions of a commercial direct imaging syringe shield containing a leaded glass window for viewing the syringe being shielded were measured. The commercial shield used is made by Nuclear Associates, Inc. and is specifically designed for use with $^{99m}$Tc radiation. The shield measurements were 58 mm length, 16.9 mm width, and 18.1 mm height. The side walls of lead were 2.5 mm thick and the bottom wall was 2.4 mm thick tapered to about 1 mm thickness at the front end (needle end). The window on the top of the shield was made of leaded glass of unsepcified density, 3.5 mm thick, 47.5 mm long, and 12.5 mm wide. "Top" as used supra refers to the location of the optical window, "Front" refers to needle location, "Back" is the plunger location, "Bottom" refers to the outside surface opposite the top and "Sides" refer to outer surfaces perpendicular to the top and bottom.

2. Theoretical Attenuation Factors

Considering the half value layer (HVL) of lead (Pb) for 150 keV radiation to be 0.31 mm, the side and bottom walls of the direct viewing shield above represent about 8 HVL's or an attenuation factor of $2^{-8} = 1/256$. Considering the build-up factor for broad beam radiation to be approximately 1.5, the net attenuation outside the sides and bottom of the shield should be $1.5/256 \approx 1/170$.

The attenuation factor for the leaded glass window depends upon the specific gravity of the lead glass used. This can vary between 2.9 to 5.9 compared to 2.4 to 2.8 for common glass and 11.35 for Pb. The HVL of pyrex glass for 150 keV radiation is about 18 mm (mass attenuation coefficient of 0.139 cm$^2$/gm and density of 2.8 g/cm$^3$) compared to the 3.5 mm thickness of the glass window. Any attenuation of radiation in the window can be assumed to occur primarily because of the lead added to the glass. If it is assumed that the leaded glass has a specific gravity of 5.8 then the density of lead in the glass would be 3 gm/cm$^3$. The HVL for this glass would then be $(11.35/3) \times 0.31$ mm which is approximately equal to 1.17 mm and the leaded glass window then corresponds to 3 HVL's with an attenuation factor of $\sim 2^{-3} = \frac{1}{8}$ or about 1/16 considering the build-up factor.

The ratio of window attenuation factor to side and bottom wall attenuation is then about 30; that is to say the radiation exposure outside the window should be about 30 times that outside the lead walls.

B. Indirect Viewing Shielding Device

1. Dimensions

Some details of the methods used in constructing the mirror shields will be given later. The length was 2.5 inches (63.5 mm) and the wall thickness was $2 \times 1.38$ mm = 2.76 mm. The angle of possible scatter from behind the mirror surface, angle B of the FIG. 9 is approximately 30°.

2. Theoretical Attenuation Factors

Considering the HVL of Pb for 150 keV radiation to be 0.31 mm, the side and bottom wall of the mirror shield represents 8.9 HVL's or about $2^{-8.9} = 1/475$ for the attenuation factor. Using again 1.5 for the build-up factor the net theoretical attenuation factor for the side and bottom walls is about 1/320.

The attenuation factor for the window is approximately 1/40. The ratio of the window attenuation factor to side and bottom wall attenuation factor is then about 8.

It is clear from the summary in Table 1 below that the two syringe shields should have comparable exposure rates outside the lead walls for the same syringe doses yet that the exposure rates outside the optical window should be significantly lower for the shielding device of the present invention.

Table 1

|  | Lead Glass Shield | Mirror Shield |
|---|---|---|
| Lead Wall Attenuation Factor | 1/170 | 1/320 |
| Optical Window Attenuation Factor | 1/6 | 1/40 |

EXPERIMENTAL COMPARISONS

A. Construction of Mirror Shield

A mirror shield was constructed using two pieces of lead sheet 1.38 mm thick which were glued together using Weld-wood contact cement in order to make sheets 2.76 mm thick. Two such sheets 2½"×2½" were made and the edges were filed and sanded to smoothness using OA4 grade flint paper. The sheets were rolled and after rolling the edges were cut even.

The inside of the shields were than painted with a white enamel paint. A mirror strip about 1.8 cm wide of mylar was applied to the inner surface of the shielding member, coated with GE Silicone Sealant, then cut to the 2½" dimension of the shield.

B. Methods of Dosimetry

Three different dosimeters were used to obtain experimental comparisons of the performance of the leaded glass window shield and the indirect viewing mirrored shielding device. The first was a standard Geiger Counter and the other two involved the more precise methods of thermo-luminescent dosimetry (TLD).

1. Geiger Counter

A Victoreen Corp. Model 490 Thyac III geiger counter with Model 489-4 side window, 30 mg/cm$^2$ thick, probe was used to get a rough estimate of the relative exposure rates at the top, bottom and sides of the shield each containing identical doses of $^{99m}$Tc radioisotope. Since the geiger tube is approximately ½" diameter and 4" long the readings represent average exposure rates over many points.

2. Thermoluminescent Dosimetry (TLD)

The more exact dosimetry techniques of thermoluminescent dosimetry give doses at virtually one point in space in the radiation field. Thermoluminescent dosimeters (TLDs) are small crystals or extruded solid crystalline materials which store a portion of the energy which they are exposed to. This energy can be "read out" in the form of light emitted when the TLDs are heated thermally. The read out device used in this study was an Eberline Corp. Model TLR-5 TLD Reader. Two types of TLDs of CaF$_2$(Dy) (TLD200) made by Harshaw Corp. and $\frac{1}{4}"\times\frac{1}{4}"\times 0.025"$ single crystals of LiF (TLD100) made by Harshaw Corp.

TLDs were fastened near the syringe shield containing approximately 15 to 20 mCi of $^{99m}$Tc. Dose was integrated for approximately one day while the $^{99m}$Tc decayed (6.05 hr half-life). The resulting readings from the TLDs were normalized to the calibrated exposing dose from the syringe.

The TLD 200 material although quite sensitive to the 140 keV and scattered gamma radiation have energy dependent responses as do geiger tubes. The TLD 100 material although less sensitive than TLD 200 is almost energy independent in its response. Table 2 gives the response for 140 keV and 74 keV (K x-rays scattered from the Pb in the shields).

Table 2

| Relative Energy Response of Dosimeters | |
|---|---|
| | Response at 74 keV/Response at 140 keV |
| Geiger Counter | 5:1 |
| CaF$_2$ (Dy) (TLD 200) extruded ribbon | 2.5:1 |
| LiF (TLD 100) cleaved single crystals | 1:1 |

To get readings, 3 to 4 CaF$_2$(Dy) dosimeters were used on the top, bottom and each side of the shields in precisely the same position relative to the syringe within each type of shield. The syringe contained precisely 1.5 ml of elucate containing $^{99m}$Tc.

For the LiF cleaved crystals only readings for the top and bottom of the shields were obtained to check that the energy dependence of the CaF$_2$(Dy) was not causing erroneously high readings for the top of the mirror shield (at the opening of the optical window) where most of the radiation was scattered K x-rays from the Pb behind the mirror surface.

C. Results

Table 3 shows the results of measuring the same $^{99m}$Tc filled syringe (containing about 1 m Ci) in each shield. The geiger tube was held transverse to the shield axis and touching the shield at the center of the geiger tube, and maximum readings were recorded.

Table 3

| | Geiger Counter (transverse to shield axis) | | |
|---|---|---|---|
| | Meter Readings (mR/hr) | | |
| Probe Position | Lead Glass Shield | Mirror Shield | Ratio of leaded glass/mirror |
| Top | 10 | 1.3 | 7.7 |
| Bottom | 0.3 | 0.4 | 0.8 |
| Left Side | 1.7 | 0.5 | 3.4 |
| Right Side | 1.7 | 0.2 | 8.5 |
| Ratio of Top to Bottom | 33 | 3.3 | |

Thus the radiation emitted through the optical windows (top) is about an order of magnitude less in the indirect shielding device (1/7.7), whereas the exposure rates at the bottom of each shield are comparable. The left and right side exposures for the leaded glass window shield appear significantly higher than that at the bottom because of the length of the geiger tube (4") which picks up radiation coming out of the window. The ratio of exposure rates at the top to exposure rates at the bottom for each shield (33 and 3.3) are in approximate agreement with the theoretical values (30 and 8) of Table 1 above.

Table 4 shows the results of measurements made using TLDs. The TLD light readouts have been normalized to the size of the exposing dose of the radioisotope.

Table 4

| TLD Readings (light units per mCi exposing dose) | | | |
|---|---|---|---|
| | Lead Glass | Mirror | Ratio of leaded window/mirror |
| CaF$_2$(Dy) TLD position | | | |
| Top | 265.4 | 41.3 | 6.43 |
| Bottom | 9.17 | 4.32 | 2.1 |
| Left Side | 2.23 | 4.10 | 0.54 |
| Right Side | 1.54 | 1.25 | 1.23 |
| Ratio of Top to Bottom | 28.9 | 9.6 | |
| LiF TLD Position | | | |
| Top | 19.0 | 0.934 | 20.3 |
| Bottom | 0.135 | 0.105 | 1.29 |
| Ratio of Top to Bottom | 141 | 8.9 | |

Again it can be seen that the radiation emitted through the optical window (top) is about an order of magnitude less in the shielding device of the present invention (1/6.43 for CaF$_2$(Dy) and 1/20.3 for LiF). Since CaF$_2$(Dy) is more sensitive for 74 keV radiation than for 140 keV radiation by a factor of 2.5 (see Table 2), the value of 1/20.3 for LiF is probably the more accurate factor by which the mirror shielding device reduces the radiation exposure rates for the shield top over that for the shield bottom are 28.9 and 9.6 for the leaded glass window and mirrored shielding device respectively using CaF$_2$(Dy). The corresponding LiF values are 141 and 8.9. The values for the mirrored shielding device are comparable to the theoretical value of 8 from Table 1; however, the LiF value for the leaded glass window shield implies that considerbly more radiation may be coming through the leaded glass window than was expected. It is possible that a glass of density lower than 5.8 g/cm$^3$ was used.

Other than for window exposure rates, the two syringe shields performed similarly as can be seen by considering the last column in Table 4. The small increase in exposure rate through the bottom of the leaded glass shield can be explained by the thinner Pb wall toward the front of the shield where it is tapered. The small increase in exposure rate through the left side of the mirrored shielding device can be explained by the possible thinning of the Pb wall due to the differential stretching of the sheet when it was shaped into the shield.

While preferred embodiments of the invention have been shown by way of example in the drawings, it will be understood that the invention is in no way limited to these embodiments.

Similarly, while the calculations in the Example are based upon $^{99m}$Tc, it will be apparent that the invention is useful for other radioactive materials and particularly for higher energy radioactive sources and materials.

Accordingly, by providing a radiation shielding device for viewing a container of radioactive material held therein, comprising a unitary envelope of a high density radiation shielding material of essentially spiral cross-section having a holding portion with a longitudinally extending aperture and a shielding portion integrally extending from one side of the aperture away from and over the line of sight through the aperture, a user may hand-hold the device to administer accurately small doses of the radioactive material without direct exposure to the radiation.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A hand-held shielding device for viewing a container of radioactive material therein, comprising a unitary envelope formed from a single sheet of a high density radiation shielding material having a holding portion shaped to surround and conform to a container, said holding portion formed with a longitudinally extending aperture extending for at least a portion of the length of said holding portion and a shielding portion extending from one side of said aperture and extending away from and at least overlapping the line of sight through said aperture, and an arcuate reflective surface on the inside surface of said shielding portion in the line of sight of said aperture and extending into said aperture of said holding portion for viewing a non-inverted image of indicia on said container whereby a user is not subject to direct radiation from said aperture.

2. The shielding device of claim 1, wherein said high density radiation shielding material is lead.

3. The shielding device of claim 1, including at least one layer of a lower energy radiation absorbing material positioned between said high density radiation shielding material and said indirect imaging means.

4. The shielding device of claim 3, wherein said lower energy radiation absorbing material is tin.

5. The shielding device of claim 1, wherein said holding portion is substantially cylindrical in shape.

6. The shielding device of claim 5, wherein said aperture extends the full length of said high density material.

7. The shielding device of claim 6, wherein said indirect imaging means is aluminized solid polymer.

8. The shielding device of claim 6, wherein said indirect imaging means is a concave mirror.

9. The shielding device of claim 6, wherein said radiation shielding material is flexible.

10. The shielding device of claim 6, wherein said radiation shielding material is rigid.

11. The shielding device of claim 6, wherein said holding means is adapted to conform to the shape of said container whereby said container is positioned securely in said device.

12. The shielding device of claim 5, wherein said indirect imaging means is a polished surface.

13. A hand-held shielding device for viewing a container of radioactive material, comprising a holding portion formed from a high density radiation shielding material shaped to surround and conform to the container with a longitudinally extending aperture extending for at least a portion of the length of said holding portion, a shielding portion extending away from and at least overlapping the line of sight through said aperture, said shielding portion pivotally mounted to said holding portion proximate said aperture for selective displacement of said shielding portion between a first closed position against said holding portion and a second open position away from said aperture for viewing the contents of the container, and indirect imaging means on the inside surface of said shielding portion in the line of sight through said aperture for viewing said container without being subject to direct radiation through said aperture.

* * * * *